United States Patent
Beaussoubre et al.

(10) Patent No.: US 9,974,323 B2
(45) Date of Patent: May 22, 2018

(54) PROCESS FOR PREPARING GRANULES COMPRISING AN ACTIVE SUBSTANCE

(71) Applicant: FIRMENICH SA, Geneva (CH)

(72) Inventors: Pascal Beaussoubre, Geneva (CH); Pierre-Etienne Bouquerand, Geneva (CH); François Meyer, Geneva (CH); Nathalie Thiebaut, Geneva (CH); Kenneth Wong, Geneva (CH)

(73) Assignee: Firmenich SA, Geneva (CH)

( * ) Notice: Subject to any disclaimer, the term of this patent is extended or adjusted under 35 U.S.C. 154(b) by 41 days.

(21) Appl. No.: 14/352,631

(22) PCT Filed: Oct. 18, 2012

(86) PCT No.: PCT/EP2012/070616
§ 371 (c)(1),
(2) Date: Apr. 17, 2014

(87) PCT Pub. No.: WO2013/057168
PCT Pub. Date: Apr. 25, 2013

(65) Prior Publication Data
US 2014/0255578 A1    Sep. 11, 2014

(30) Foreign Application Priority Data
Oct. 21, 2011    (EP) .................................... 11186226

(51) Int. Cl.
| | |
|---|---|
| A23L 1/22 | (2006.01) |
| A23L 1/222 | (2006.01) |
| A61Q 13/00 | (2006.01) |
| A61K 8/25 | (2006.01) |
| A61K 8/73 | (2006.01) |
| A61K 8/02 | (2006.01) |
| C11D 3/22 | (2006.01) |
| C11D 3/50 | (2006.01) |
| C11D 11/02 | (2006.01) |
| C11B 9/00 | (2006.01) |
| B01J 2/04 | (2006.01) |
| A23L 27/10 | (2016.01) |
| A23L 27/12 | (2016.01) |

(52) U.S. Cl.
CPC ............. *A23L 1/2225* (2013.01); *A23L 27/11* (2016.08); *A23L 27/13* (2016.08); *A61K 8/0225* (2013.01); *A61K 8/0241* (2013.01); *A61K 8/25* (2013.01); *A61K 8/73* (2013.01); *A61Q 13/00* (2013.01); *B01J 2/04* (2013.01); *C11B 9/00* (2013.01); *C11D 3/222* (2013.01); *C11D 3/505* (2013.01); *C11D 11/02* (2013.01); *A61K 2800/412* (2013.01); *A61K 2800/56* (2013.01); *A61K 2800/84* (2013.01)

(58) Field of Classification Search
CPC ........ A23L 1/2225; A23L 27/11; A23L 27/13; A61Q 13/00; A61K 8/25; A61K 8/73; A61K 8/0225; A61K 8/0241; A61K 2800/412; A61K 2800/56; A61K 2800/84; C11D 3/222; C11D 3/505; C11D 11/02; C11B 9/00; B01J 2/04
USPC ................ 426/443, 465, 471, 534, 536, 650
See application file for complete search history.

(56) References Cited

U.S. PATENT DOCUMENTS

| | | | |
|---|---|---|---|
| 2004/0208981 A1* | 10/2004 | Wong ............................. | 426/659 |
| 2007/0078071 A1* | 4/2007 | Lee et al. ...................... | 510/130 |
| 2009/0253612 A1 | 10/2009 | Mushock et al. | |

FOREIGN PATENT DOCUMENTS

| | | |
|---|---|---|
| WO | WO2007/054853 A1 | 5/2007 |
| WO | WO2007/135583 A2 | 11/2007 |

OTHER PUBLICATIONS

Hidefumi et al., Innovative Food Science & Emerging Technologies 2 (2001) 55-61.
Dickinson, Trends in Food Science & Technology 24 (2012) 4-12.

\* cited by examiner

*Primary Examiner* — Leslie Wong
(74) *Attorney, Agent, or Firm* — Winston & Strawn LLP

(57) ABSTRACT

The present invention relates to granules comprising an active substance, obtained by spray-drying an emulsion comprising said active substance, solid particles, water and a water-soluble biopolymer having a molecular weight below 100 KDa. The invention further relates to a process for obtaining such granules and to products containing them.

14 Claims, 2 Drawing Sheets

PROCESS FOR PREPARING GRANULES COMPRISING AN ACTIVE SUBSTANCE

TECHNICAL FIELD

The present invention relates to granules comprising an active substance, obtained by spray-drying an emulsion comprising said active substance, solid particles, water and a water-soluble biopolymer having a molecular weight below 100 KDa. The invention further relates to a process for obtaining such granules and to products containing them.

PRIOR ART

Spray-drying is a well known technique for the encapsulation of flavours and fragrances. Spray-dried granules are commonly prepared from an emulsion that is sprayed into a drying chamber. The emulsion typically comprises an active substance such as a flavour or a fragrance, a carrier and an emulsifier.

Most of the time, biopolymers with surface active properties, such as for example gum arabic, modified starches, modified cellulose, gelatine, alginates or even proteins such as albumin or beta-globulin, are used as carriers.

For example, US 2009/0253612 describes a spray-dry encapsulation process for flavour or fragrance comprising drying an aqueous emulsion containing the oil to be encapsulated, modified starch and phosphate salts.

When other types of carriers are used at least one emulsifier is used in addition to the carrier. For example, Hidefumi et al., Innovative Food Science & Emerging Technologies, 2 (2001), pp. 55-61, discloses a process for the microencapsulation of emulsified ethyl butyrate by spray-drying using maltodextrin as carrier and gum arabic as emulsifier.

A number of emulsion parameters influence the quality of the spray-dried solid granules. The flavour or fragrance load in the granules, which is essential to achieve satisfying perceived intensity of the active substance in the final application depends in particular on the encapsulation yield which is defined as the amount of flavour or fragrance actually encapsulated in the granules, compared to the theoretical amount that could be present if no flavour or fragrance was lost during the spray-drying process.

It is therefore desirable to provide granules obtained from emulsions having a high proportion of droplets of active substance and to limit as much as possible the loss of active substance, especially when it is a volatile active substance, during the drying step of the process.

Another important parameter of the emulsion to be spray-dried is the dispersion of the active substance in the aqueous phase. It would therefore be advantageous to provide a system allowing a good dispersion of the active in the carrier and water.

The behaviour of the spray-dried granules when they are re-dissolved in water also determines their quality. It is firstly desirable that the granules have a good dispersion in water, so as to form a clear suspension or solution. Secondly, the way the granules are capable of releasing the active substance to the headspace when they are dissolved in water is also an essential characteristic of spray-dried granules. A particularly advantageous release profile is that wherein the release of the active substance is to maintained and controlled for a long period.

It would therefore be desirable to provide a new encapsulation process for producing granules in which a high active substance load is achieved in the dry granules even with volatile substances, the obtained granules forming clear solutions or suspensions when redispersed in water and releasing in a suitable way the active substance to the headspace when dissolved in water.

It would further be useful to avoid the presence of polymeric emulsifiers in the spray-dried emulsion.

To the best of our knowledge none of the spray-dried granules described in the prior art solves these problems.

SUMMARY OF THE INVENTION

Figure 1:
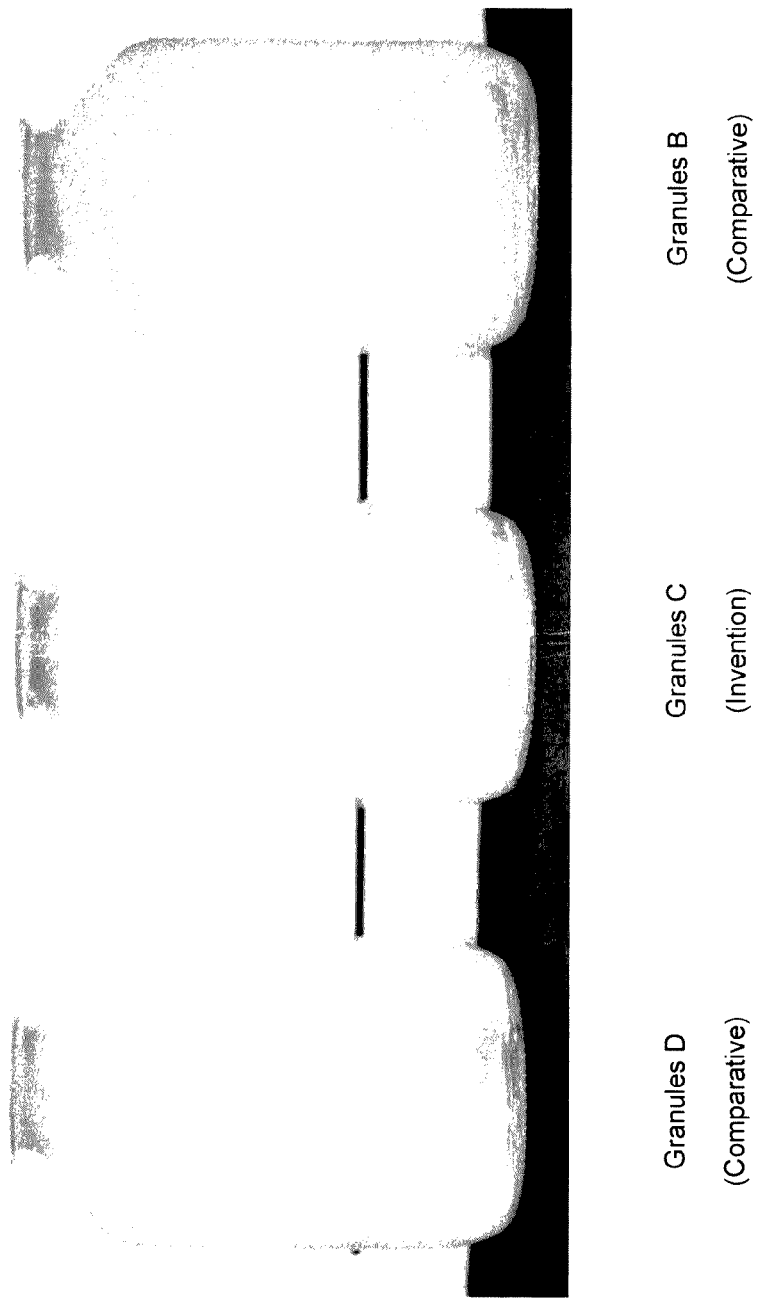
FIG. 1: Aspect of dispersion of Granules B, C and D during the first 2 hours after re-dispersion of the granules in water.

Accordingly, the invention relates to a process for preparing granules, the process comprising the steps of:
a) preparing an emulsion comprising
   i. an active substance;
   ii. a water soluble biopolymer having a molecular weight below 100 KDa and devoid of emulsifying properties;
   iii. solid particles that are insoluble in water; and
   iv. water;
b) spray-drying the emulsion obtained in step a) so as to obtain granules.

In another aspect, the invention relates to spray-dried granules comprising
   i. an active substance;
   ii. a water soluble biopolymer having a molecular weight below 100 KDa and devoid of emulsifying properties; and
   iii. solid particles that are insoluble in water.

In a further aspect the invention relates to a consumer product comprising the granules of the invention.

DETAILED DESCRIPTION OF THE INVENTION

The present inventors have surprisingly discovered that when an emulsion intended to be spray dried is prepared with solid particles instead of a surfactant or polymeric emulsifier, the active substance loss during the drying step is low, even if the active substance is volatile, such as flavours or fragrance compounds. The proportion of active substance droplets in such emulsion can be high, so that high loads of active substance in the final granules can be obtained. It was also surprisingly discovered that the release of the perfume or fragrance from the granules of the invention is particularly advantageous, because a long-lasting release of the active to the headspace is observed when the granules are re-dispersed in water.

In the first step of the process of the invention an emulsion is prepared comprising
   i. an active substance;
   ii. a water soluble biopolymer having a molecular weight below 100 KDa and devoid of emulsifying properties;
   iii. solid particles that are insoluble in water; and
   iv. water.

The active substance can be an ingredient alone or a mixture of active ingredients. Preferably, the active substance comprises at least 90% by weight, relative to the total weight of the active substance, of compounds having a log P of at least 1, more preferably it comprises at least 90% by weight of ingredients having a log P of at least 2. Even more preferably, the active substance comprises at least 99% by weight, relative to the total weight of the active substance, of ingredients having a log P of at least 1, most preferably it comprises at least 99% by weight of ingredients having a log P of at least 2. For the purpose of the present invention log P is defined as the calculated log P as obtained by calculation using the EPI suite v3.10, 2000, U.S. Environmental Protection Agency.

In a preferred aspect of the invention, the active substance is selected from flavours and fragrances. For the purpose of the present invention, the terms "flavour or fragrance" encompass flavour or fragrance ingredients or compositions of current use in the flavour and/or fragrance industry, of both natural and synthetic origin. It includes single compounds and mixtures. Specific examples of such flavour or fragrance ingredients may be found in the current literature, e.g. in Fenaroli's Handbook of flavour ingredients, 1975, CRC Press; Synthetic Food adjuncts, 1947 by M. B. Jacobs, edited by Van Nostrand; or Perfume and Flavor Chemicals by S. Arctander, 1969, Montclair, N.J. (USA). Many other examples of current flavouring and/or perfuming ingredients may be found in the patent and general literature available. The flavouring or perfuming ingredients may be present in the form of a mixture with solvents, adjuvants, additives and/or other components, generally those of current use in the flavours and fragrance industry.

"Flavouring ingredients" are well known to a person skilled in the art of aromatising as being capable of imparting a flavour or taste to a consumer product, or of modifying the taste and/or flavour of said consumer product, or yet its texture or mouthfeel.

By "perfuming ingredients" it is understood here compounds which are used as active ingredients in perfuming preparations or compositions in order to impart a hedonic effect when applied to a surface. In other words, such compounds, to be considered as being perfuming ones, must be recognized by a person skilled in the art of perfumery as being able to impart or modify in a positive or pleasant way the odor of a composition or of an article or surface, and not just as having an odor. Moreover, this definition is also meant to include compounds that do not necessarily have an odor but are capable of modulating the odor of a perfuming composition, perfumed article or surface and, as a result, of modifying the perception by a user of the odor of such a composition, article or surface. It also contains malodor counteracting ingredients and compositions. By the term "malodor counteracting ingredient" we mean here compounds which are capable of reducing the perception of malodor, i.e. of an odor that is unpleasant or offensive to the human nose by counteracting and/or masking malodors. In a particular embodiment, these compounds have the ability to react with key compounds causing known malodors. The reactions result in reduction of the malodor materials' airborne levels and consequent reduction in the perception of the malodor.

Accordingly, in an embodiment, the active substance comprises at least 5 wt. %, preferably at least 10. %, preferably at least 20%, more preferably at least 30% and most preferably at least 40% of chemical compounds having a vapour pressure of at least 0.007 Pa at 25° C., preferably at least 0.1 Pa at 25° C., more preferably at least 1 Pa at 25° C. and most preferably at least 10 Pa at 25° C., all percentages being defined by weight relative to the total weight of the active substance. Compounds meeting these criteria are generally regarded as having a volatile character and therefore have an odor or flavour. The method of the present invention therefore allows efficient encapsulation of high amounts of volatile ingredients. In a preferred embodiment of the invention, the active substance does not comprise any compound that remains odorless due to a volatility below any of the above-mentioned thresholds.

For the purpose of the present invention the vapour pressure is determined by calculation. Accordingly, the method disclosed in "EPI suite"; 2000 U.S. Environmental Protection Agency, is used to determine the value of the vapour pressure of a specific compound or component of the active substance.

The amount of active substance in the emulsion is preferably comprised between 5 and 67% by weight, more preferably between 10 and 40% by weight, relative to the total weight of the emulsion. This concentration corresponds to a concentration of the active substance of from 10 to 90%, more preferably from 15 to 60% by weight, relative to the total weight of the granules (dry weight).

Any water soluble biopolymer with a molecular weight below 100 KDa and devoid of emulsifying properties can be used for the purpose of the invention.

A "water soluble biopolymer" is intended for the purpose of the present invention as encompassing any biopolymer which forms a one-phase solution in water. Preferably, it forms a one phase solution when dissolved in water at concentrations as high as 20% by weight, more preferably even as high as 50% by weight. Most preferably it forms a one phase solution when dissolved in water at any concentration.

As "biopolymer devoid of emulsifying properties", it is intended for the purpose of the present invention polymers that are not surface active and are devoid of barrier and emulsifying properties. Suitable biopolymers devoid of emulsifying properties are soluble in water and are devoid of hydrophobic groups. Examples of biopolymers that are considered as having emulsifying properties and that are preferably excluded comprise gum Arabic, gelatine, modified starch such as octenylsuccinated starch E1450 (Capsul™ Hicap™, Puritygum™, Emcap™ etc.), modified cellulose such as ethylcellulose, hydroxypropylcellulose or hydroxypropylmethylcellulose. Such polymers are avoided because they would affect the particular release profile of volatiles from the granules of the present invention.

Preferred water soluble biopolymers are biopolymers like polysaccharides, oligosaccharides and disaccharides. Preferred polysaccharides are starch hydrolysates with a dextrose equivalent above 2 and most preferred ones are selected from dextrins, maltodextrins and corn-syrup. The most preferred biopolymer for use in the present invention is maltodextrin.

It is also particularly advantageous to use water soluble biopolymers which do not comprise any chemical substitution, meaning that the water soluble biopolymer has not been chemically (i.e. artificially) modified.

The water soluble biopolymer is preferably used in an amount of from 10 to 70% by weight, more preferably from 30 to 55% by weight, relative to the total weight of the emulsion. These concentrations are defined so as to maintain the viscosity of the emulsion below 400 Pa, which is a preferred range of viscosity in spray-drying processes.

The solid particles used in the emulsion are defined as any solid particle that is insoluble in water. A particle is considered as insoluble in water if its solubility is lower than 0.5% by weight.

Preferred particles are those having an average diameter of at most 3 μm, more preferably of at most 500 nm.

Preferred solid particle types include the following:
- silicon oxides, such as silica (e.g. colloidal silica such as that sold under the tradename Klebosol® by AZ Electronic Materials) or silicates (e.g. synthetic silicate such as that sold under the tradename Laponite® by Rockwood Additives);
- metal oxides, hydroxides, salts of inorganic or organic acids and their mixtures (e.g. $TiO_2$, FeO, $Fe(OH)_2$, $FeCO_3$; MgO, $Mg(OH)_2$, $MgCO_3$, $Mg_3(PO4)_2$; $CaCO_3$, $CaSO_4$, $Ca_5(PO4)_3(OH)$, $Ca_3(C_6H_5O_7)_2$);
- silver nanoparticles;
- magnesium and aluminium silicates (clays);
- latexes;
- dietary fibers such as microcrystalline cellulose, lignin and chitin;
- cells (e.g. yeast cells) or fragments thereof;
- humic acid;
- enteric polymers (such as for example Eudragit® FS 30 D and Eudragit® L 100-55 from Evonik); and
- crystals of fats or fatty acids.

Mixtures of such particle types can also be used. More preferably, the solid particle is selected from
- silicon oxides, such as silica (e.g. colloidal silica such as that sold under the tradename Klebosol® by AZ Electronic Materials) or silicates (e.g. synthetic silicate such as that sold under the tradename Laponite® by Rockwood Additives);
- metal oxides, hydroxides, salts of inorganic or organic acids and their mixtures (e.g. $TiO_2$, FeO, $Fe(OH)_2$, $FeCO_3$; MgO, $Mg(OH)_2$, $MgCO_3$, $Mg_3(PO4)_2$; $CaCO_3$, $CaSO_4$, $Ca_5(PO4)_3(OH)$, $Ca_3(C_6H_5O_7)_2$);
- silver nanoparticles;
- cells (e.g. yeast cells) or fragments thereof; and
- dietary fibers such as microcrystalline cellulose, dextins, lignin and chitin.

Most preferably, the solid particle is silica (e.g. colloidal silica such as that sold under the tradename Klebosol® by AZ Electronic Materials).

In a preferred aspect of the invention, the active substance is hydrophobic, as defined by a log P above 1, more preferably above 2, and the solid particle is hydrophilic, i.e. it disperses easily in water to form a homogeneous suspension of particles. Preferably, in the emulsion, the particle will form with the oil and the water a contact angle $\theta \leq 90°$, more preferably $10° \leq \theta \leq 90°$. The contact angle $\theta$ is the three-phase contact angle, measured through the aqueous phase, that is made by an interface of water and oil on the particle's surface. Practically, when the contact angle is comprised within the above range the particle succeeds in making an oil in water emulsion. It is well-known in the field of colloids that the contact angle is a quantification of the wettability of the particles at an interface oil/water. A more detailed definition of the contact angle can be found in Dickinson, E., *Use of nanoparticles and microparticles in the formation and stabilization of food emulsions*, Trends in Food Science & Technology (2011).

The relative ratio of solid particles, relative to the active substance is preferably comprised between 1:1 and 1:30. In another preferred embodiment, the solid particles are present in an amount of from 0.1 to 30%, preferably from 0.5 to 30% more preferably from 1 to 16% by weight, relative to the total weight of the emulsion.

In a preferred aspect of the invention, the amount of water in the emulsion is comprised between 20 and 80% by weight, relative to the total weight of the emulsion.

The emulsion may also contain optional ingredients. It may in particular further contain an effective amount of a fireproofing or explosion suppression agent. The type and concentration of such agents in spray-drying emulsions is known to the person skilled in the art. One can cite as non-limiting examples of such fireproofing or explosion suppression agents inorganic salts, $C_1$-$C_{12}$ carboxylic acids, salts of $C_1$-$C_{12}$ carboxylic acids and mixtures thereof. Preferred explosion suppression agents are, salicylic acid, acetic acid, propionic acid, butyric acid, isobutyric acid, valeric acid, caproic acid, citric acid, succinic acid, hydroxysuccinic acid, maleic acid, fumaric acid, oxylic acid, glyoxylic acid, adipic acid, lactic acid, tartaric acid, ascorbic acid, the potassium, calcium and/or sodium salts of any of the aforementioned acids, and mixtures of any of these.

Other optional ingredients include antioxidants, preservatives, colorants and dyes.

The emulsion can be formed using any known emulsifying method, such as high shear mixing, sonication or homogenization. Such emulsifying methods are well known to the person skilled in the art.

Preferably the emulsion is free of emulsifiers.

The droplet size d(v,0.9) of the emulsion is preferably comprised between 0.5 and 15 µm, more preferably between 0.5 and 10 µm.

In step b), the emulsion is spray-dried so as to obtain granules.

The emulsion is first subjected to a spraying step during which the emulsion is dispersed in the form of drops into a spraying tower. Any device capable of dispersing the emulsion in the form of drops can be used to carry out such dispersion. For instance, the emulsion can be guided through a spraying nozzle or through a centrifugal wheel disk. Vibrated orifices may also be used.

In one aspect of the invention the emulsion is dispersed in the form of drops into a cloud of powdering agent present in the dry tower. Such type of process is for example described in details in WO2007/054853 or in WO2007/135583.

For a specific formulation, the size of the granules is influenced by the size of the drops that are dispersed into the tower. When a spraying nozzle is used for dispersing the drops, the size of such drops can be controlled by the flow rate of an atomising gas through the nozzle, for example. In the case where a centrifugal wheel disk is used for dispersal, the main factor for adjusting droplet size is the centrifugal force with which the drops are dispersed from the disk into the tower. The centrifugal force, in turn, depends on the speed of rotation and the diameter of the disk. The feed flow rate of the emulsion, its surface tension and its viscosity are also parameters controlling the final drop size and size distribution. By adjusting these parameters, the skilled person can control the size of to the drops of the emulsion to be dispersed in the tower.

Once sprayed in the chamber, the droplets are dried using any technique known in the art. These methods are perfectly documented in the patent and non-patent literature in the art of spray-drying. For example, Spray-Drying Handbook, 3$^{rd}$ ed., K. Masters; John Wiley (1979), describes a wide variety of spray-drying methods.

The process of the present invention may be performed in any conventional spraying tower. A conventional multi-stage drying apparatus is for example appropriate for conducting the steps of this process. It may comprise a spraying tower, and, at the bottom of the tower, a fluidised bed intercepting partially dried granules after falling through the tower.

The amount of flavour or fragrance lost during the spray drying step is preferably below 15%, more preferably below 10%, most preferably below 5%, these percentages being defined by weight, relative to the theoretical amount that would be present in the granules if there was absolutely no flavour or fragrance lost during the spray-drying step.

The spray-dried granules of the present invention typically comprise
i. an active substance;
ii. a water soluble biopolymer having a molecular weight below 100 KDa and devoid of emulsifying properties;
iii. solid particles that are insoluble in water; and
iv. water.

All components of the granules are as defined above.

The granules of the invention may also comprise residual amounts of water, but typically less than 15%, preferably less than 10%, more preferably less than 2% by weight, relative to the total weight of the granules.

Preferably such granules are obtainable and/or obtained by the process described in any of the above embodiments of the invention.

In a preferred aspect of the invention the size of the granules is typically of at least 10 µm, preferably at least 20 µm. Depending on the process used for spray-drying, in particular when a powdering agent is present in the drying tower, as described above, the dry granules can have an average size of up to 300 or even up to 750 µm. In a preferred embodiment of the invention, the average size of the granules is at least 5 times larger than the average size of the oil droplets in the emulsion.

In another aspect, the invention relates to a consumer product comprising the to granules of the invention. Preferably such product is a flavoured or fragranced product.

Preferably, the flavoured product is a food product. The consumer product of the invention preferably is a particulate or powdery flavoured or fragranced product. In such a case, the granules of the invention may easily be added thereto by dry-mixing.

In a preferred aspect of the invention, the food product is selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

In an embodiment the fragranced product is a powdery product. Preferably it is a powder or a tablet detergent, a deodorant or an antiperspirant. In another embodiment, it is a body care product and most preferably it is a deodorant or an antiperspirant.

The granules of the present invention have the advantage of being well dispersed in aqueous media and in particular in consumer product bases comprising water.

EXAMPLES

The invention will now be described in further detail by way of the following examples.

Example 1

Preparation of Granules According to the Invention

Emulsion A was prepared having the following ingredients:

TABLE 1

Composition of Emulsion A

| Ingredient | Parts by weight [%] |
| --- | --- |
| Flavour[1] | 17.65 |
| Water soluble biopolymer[2] | 41.17 |
| Solid particles[3] | 3.17 |
| Citric acid | 0.12 |
| Antibacterial agent[4] | 0.02 |
| Water | 37.87 |
| Total | 100 |

[1]Lemon oil, origin: Firmenich SA, Geneva, Switzerland
[2]Glucidex ® 18 DE (Maltodextrin, origin: Roquette Frères)
[3]Klebosol ® 30V25 (suspension of colloidal silica), origin: AZ Electronic Materials
[4]Potassium sorbate and sodium benzoate.

Lemon oil (30 g) was added to a dispersion of 18 g of Klebosol® in 52 g of distilled water containing the antibacterial agent. The pH was adjusted to 3 by addition of citric acid. The to resulting mixture was homogenized using an ultrasonic probe in cold conditions (water bath with ice). The average size of the oil droplets was visually checked by microscopy to be around 3 µm. The obtained emulsion was then blended using a propeller type mixer with 70 g of Glucidex®.
Granules A were prepared by spray-drying Emulsion A using a Buchi Mini Spray-Dryer B-290, supplied by Büchi, Flawil, Switzerland, with an air inlet temperature set to 180° C. and a throughput set to 500 ml per hour. The air outlet temperature was of 90° C. The emulsion before atomization was at ambient temperature.
The lemon oil content in the spray-dried granules was measured by LF-NMR using the proper calibration. The encapsulation efficiency was estimated by measuring the amount of oil in the granules and comparing with the theoretical content that would be achieved without any loss during the spray-drying process. The amount of lemon oil lost was less than 5%, the final loading of lemon oil in the granules being about 28.4% by weight, relative to the total weight of the granules.

Example 2

Preparation of Granules with Modified Starch as Emulsifier (Comparative Example)

Emulsion B was prepared having the following ingredients:

TABLE 2

Composition of Emulsion B

| Ingredient | Parts by weight [%] |
| --- | --- |
| Flavour[1] | 15.00 |
| Water soluble biopolymer[2] | 31.50 |

TABLE 2-continued

Composition of Emulsion B

| Ingredient | Parts by weight [%] |
|---|---|
| Emulsifier[3] | 3.50 |
| Antibacterial agent[4] | 0.02 |
| Water | 49.98 |
| Total | 100 |

[1] Lemon oil (origin: Firmenich SA, Geneva, Switzerland)
[2] Glucidex ® 18 DE (Maltodextrin, origin: Roquette Frères)
[3] Hi-Cap ®100 (modified starch), origin: National Starch
[4] Potassium sorbate and sodium benzoate.

Emulsion B was prepared using the same protocol as described in Example 1, except that the solid particles were replaced by the emulsifier.

The average size of the oil droplets was visually checked by microscopy and measured by granulometry (Malvern Nanosizer) to be almost the same as for Emulsion A, i.e. about 3 μm.

Granules B were prepared following the same protocol as described in Example 1.

Also following the same protocol as in Example 1, the amount of lemon oil lost during the spray-drying process was measured. About 11% of the oil was lost, leading to a final oil loading in Granules B of about 26.6% wt.

The ratio solid material/active (oil) being comparable in both Examples 1 and 2, the main difference between these two examples is the use of solid particles instead of a polymeric emulsifier. Comparison of these two example shows that less flavor (lemon oil) is lost under similar conditions of formulation and process when the spray-dried emulsion comprises a solid particle (silica) instead of an usual emulsifier (modified starch), which further results in an improved oil loading in the spray-dried granules of the invention compared to the prior art ones.

The average size of the obtained spray-dried granules was about 50 μm, as estimated by microscopy.

Example 3

Preparation of Granules According to the Invention

Emulsion C was prepared having the following ingredients:

TABLE 3

Composition of Emulsion C

| Ingredient | Parts by weight [%] |
|---|---|
| Flavour[1] | 20.69 |
| Water soluble biopolymer[2] | 31.03 |
| Solid particles[3] | 1.86 |
| Citric acid | 0.14 |
| Antibacterial agent[4] | 0.02 |
| Water | 46.26 |
| Total | 100 |

[1] Lemon oil (origin: Firmenich)
[2] Glucidex ® 18 DE (Maltodextrin, origin: Roquette Frères)
[3] Klebosol ®30V25 (suspension of colloidal silica), origin: AZ Electronic Materials)
[4] Potassium sorbate and sodium benzoate.

Emulsion C was prepared using the same protocol as in example 1, only the amount of each ingredient being different. Granules C were then prepared by spray-drying of Emulsion C using the process described in Example 1.

Example 4

Preparation of Granules with Modified Starch as Emulsifier (Comparative Example)

For comparative study, Emulsion D was prepared having the following ingredients:

TABLE 4

Composition of Emulsion D

| Ingredient | Parts by weight [%] |
|---|---|
| Flavour[1] | 20.00 |
| Water soluble biopolymer[2] | 27.00 |
| Emulsifier[3] | 3.00 |
| Antibacterial agent[4] | 0.02 |
| Water | 49.98 |
| Total | 100 |

[1] Lemon oil (origin: Firmenich)
[2] Glucidex ® 18 DE (Maltodextrin, origin: Roquette Frères)
[3] Capsul ™ (modified starch), origin: National Starch
[4] Potassium sorbate and sodium benzoate.

Emulsion D was prepared using the same protocol as in example 2, only the amount of each ingredient being different. Granules D were then prepared by spray-drying Emulsion D using the process disclosed in Example 1.

Example 5

Re-Dispersion of the Granules of the Invention in Water

Based on the lemon oil loading of Granules B, C and D, the granules were re-dispersed in demineralised water using magnetic stirrer to reach a final concentration of lemon oil of 0.005% by weight, relative to the total weight of the dispersion.

The turbidity of the obtained dispersion was assessed visually. Surprisingly the re-dispersion in water of the granules of the invention (Granules C, stabilized by solid particles) led immediately to a clear, almost transparent solution. By comparison the solutions were optically turbid when comparative Granules B and D were re-dispersed in water. The aspect of the dispersions remained the same for two hours (see FIG. 1). The ability of the capsules of the present invention to re-disperse quickly in water to provide a clear dispersion is very advantageous, in particular in applications where transparency is generally needed, for example in beverages.

Example 6

Volatile Compound Release from Granules of the Invention

Granules C and D were re-dispersed in demineralised water to reach a final concentration of lemon oil of 0.5% by weight relative to the total weight of the dispersion in both cases. The release profile of limonene, the main component of lemon oil, was measured over time in the headspace above each solution in identical conditions of analysis. Static headspace was performed at 32° C. as a reference for the concentration in limonene ($P_0'$). Headspace measurements were performed in dynamic conditions under 45 ml/min nitrogen flow at 32° C. (P'). Measurements were performed in triplicate.

Figure 2:
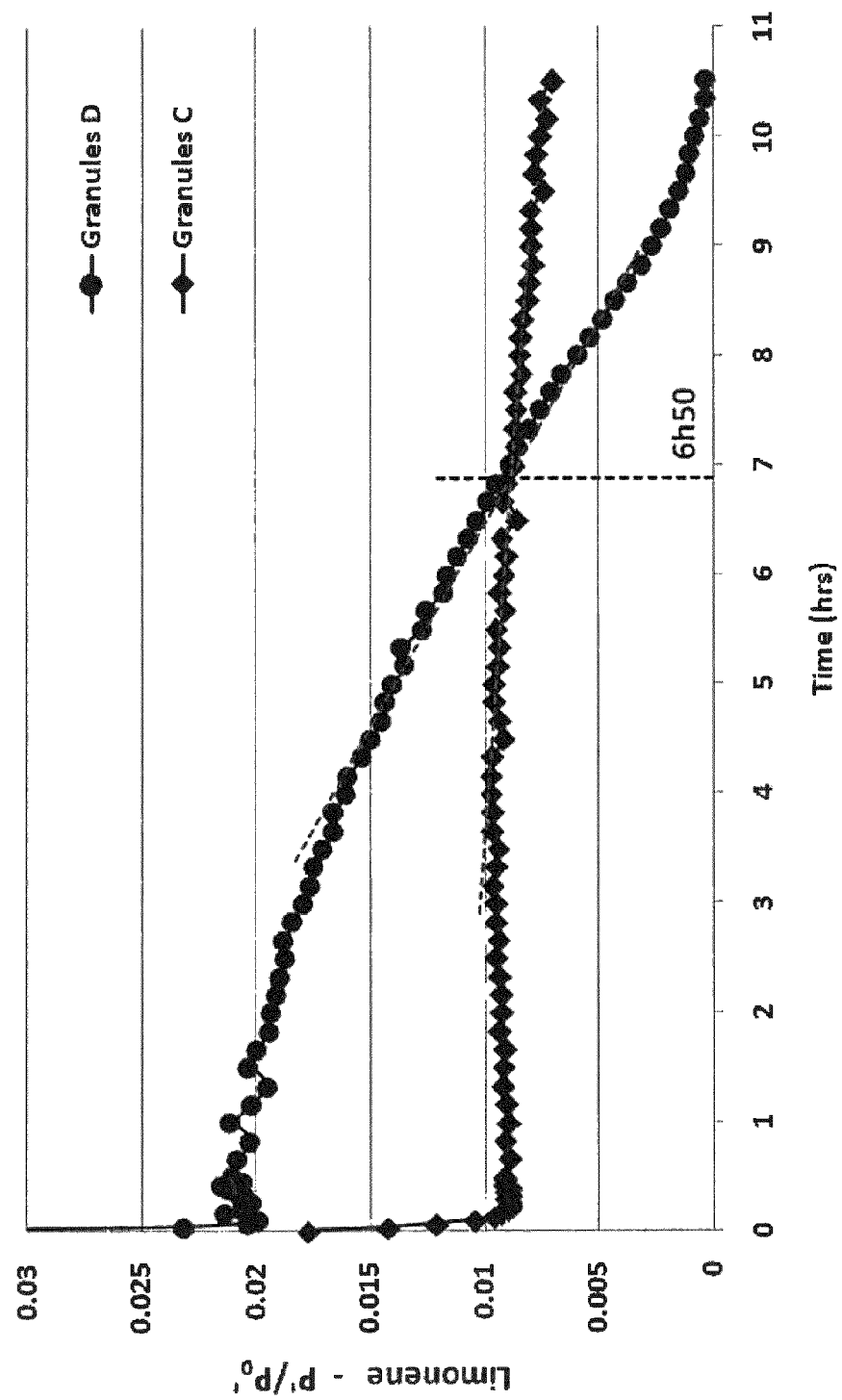
FIG. 2: Release profile of limonene in the headspace above the re-dispersions in water of Granules C (diamonds) and Granules D (circles).

As shown in FIG. 2, the limonene release from Granules D (comparative) is an almost linear decrease of limonene concentration in the gas as a function of time. In comparison, for Granules C (invention) a strong decrease is observed for the first 10 minutes, followed by a strong inflexion point and a more constant concentration of limonene in the gas for the 10 hours of the analysis.

The consequence of this difference in release profile it that after about seven hours, the amount of limonene in the headspace above re-dispersion of Granules D (comparative) is lower than that in the headspace above re-dispersion of Granules C (invention). The controlled release from the granules of the invention, thus leads to a long-lasting effect that is advantageous for flavours and for perfumery applications such as antiperspirants or body care applications.

Example 7

Preparation of Granules from a Standard Pickering Emulsion (Comparative)

Emulsion E was prepared having the following ingredients:

TABLE 5

Composition of Emulsion E

| Ingredient | Parts by weight [%] |
|---|---|
| Flavour[1] | 30.00 |
| Solid particles[2] | 2.70 |
| Citric acid | 0.20 |
| Antibacterial agent[3] | 0.04 |
| Water | 67.06 |
| Total | 100 |

[1]Lemon oil (origin: Firmenich)
[2]Klebosol ®30V25 (suspension of colloidal silica), origin: AZ Electronic Materials)
[3]Potassium sorbate and sodium benzoate.

Emulsion E was prepared using the same protocol as described in Example 1, except that the water-soluble biopolymer was not added.

Granules E were then prepared following the same protocol as in Example 1. Also following the same protocol as in Example 1, the amount of lemon oil lost during to the spray-drying process was measured. About 84.4% of the oil was lost, leading to a final oil loading in Granules E of about 4.69% wt.

This example clearly shows the advantage of the present invention over spray-drying of emulsions stabilized by solid particles but containing no water-soluble biopolymer, such emulsions being unable to protect volatile substances during the drying step.

Example 8

Preparation of Granules According to the Invention

Emulsion F was prepared having the following ingredients:

TABLE 6

Composition of Emulsion F

| Ingredient | Parts by weight [%] |
|---|---|
| Flavour[1] | 17.65 |
| Water soluble biopolymer[2] | 41.18 |
| Solid particles[3] | 0.41 |
| Citric acid | 0.06 |
| Antibacterial agent[4] | 0.01 |
| Water | 40.69 |
| Total | 100 |

[1]Lemon oil (origin: Firmenich)
[2]Glucidex ® 18 DE (Maltodextrin, origin: Roquette Frères)
[3]Natpure Cellgum (microcrystalline cellulose, origin: Sensient Technologies LCW)
[4]Potassium sorbate and sodium benzoate.

Emulsion F was prepared using the same protocol as in example 1, only the type of solid particles and the amount of each ingredient being different. Granules were then prepared by spray-drying of Emulsion F using the process described in Example 1.

Example 9

Preparation of Granules According to the Invention

Emulsion G was prepared having the following ingredients:

TABLE 7

Composition of Emulsion G

| Ingredient | Parts by weight [%] |
|---|---|
| Flavour[1] | 17.65 |
| Water soluble biopolymer[2] | 41.18 |
| Solid particles[3] | 1.65 |
| Citric acid | 0.18 |
| Antibacterial agent[4] | 0.01 |
| Water | 39.34 |
| Total | 100 |

[1]Lemon oil (origin: Firmenich)
[2]Glucidex ® 18 DE (Maltodextrin, origin: Roquette Frères)
[3]Laponite ®RD (synthetic layered silicate, origin: Rockwood Additives)
[4]Potassium sorbate and sodium benzoate.

Emulsion G was prepared using the same protocol as in example 1, only the type of solid particles and the amount of each ingredient being different. Granules were then prepared by spray-drying of Emulsion G using the process described in Example 1.

Example 10

Preparation of Granules According to the Invention

Emulsion H was prepared having the following ingredients:

TABLE 8

Composition of Emulsion H

| Ingredient | Parts by weight [%] |
|---|---|
| Flavour[1] | 17.65 |
| Water soluble biopolymer[2] | 41.18 |
| Solid particles[3] | 0.41 |
| Citric acid | 0.06 |
| Antibacterial agent[4] | 0.01 |
| Water | 40.69 |
| Total | 100 |

[1] Lemon oil (origin: Firmenich)
[2] Glucidex ® 18 DE (Maltodextrin, origin: Roquette Frères)
[3] Humic acid (origin: Fluka)
[4] Potassium sorbate and sodium benzoate.

Emulsion H was prepared using the same protocol as in example 1, only the type of solid particles and the amount of each ingredient being different. Granules were then prepared by spray-drying of Emulsion H using the process described in Example 1.

Example 11

Preparation of Granules According to the Invention

Emulsion I was prepared having the following ingredients:

TABLE 9

Composition of Emulsion I

| Ingredient | Parts by weight [%] |
|---|---|
| Flavour[1] | 17.65 |
| Water soluble biopolymer[2] | 41.18 |
| Solid particles[3] | 0.41 |
| Antibacterial agent[4] | 0.01 |
| Water | 40.75 |
| Total | 100 |

[1] Lemon oil (origin: Firmenich)
[2] Glucidex ® 18 DE (Maltodextrin, origin: Roquette Frères)
[3] Eudragit ®L100-55 (Methacrylic acid - Ethylacrylate copolymer, origin: Evonik)
[4] Potassium sorbate and sodium benzoate.

Emulsion I was prepared using the same protocol as in example 1, only the type of solid particles and the amount of each ingredient being different. Eudragit® L100-55 was insoluble in water in the conditions of emulsification. Granules were then prepared by to spray-drying of Emulsion I using the process described in Example 1.

Example 12

Preparation of Granules According to the Invention

Emulsion J was prepared having the following ingredients:

TABLE 10

Composition of Emulsion J

| Ingredient | Parts by weight [%] |
|---|---|
| Flavour[1] | 17.647 |
| Water soluble biopolymer[2] | 41.176 |
| Solid particles[3] | 0.412 |
| Sodium hydroxide | 0.001 |
| Antibacterial agent[4] | 0.012 |
| Water | 40.752 |
| Total | 100 |

[1] Lemon oil (origin: Firmenich)
[2] Glucidex ® 18 DE (Maltodextrin, origin: Roquette Frères)
[3] Latex particles (crosslinked copolymer of Methylmethacrylate - methacrylic acid and 1,4-bis(vinyloxy)butane, origin: Firmenich)
[4] Potassium sorbate and sodium benzoate.

Emulsion J was prepared using the same protocol as in example 1, only the type of solid particles and the amount of each ingredient being different. Latex particles were insoluble in water in the conditions of emulsification. Granules were then prepared by spray-drying of Emulsion J using the process described in Example 1.

Examples 1, 3 and 8-12 demonstrate the wide variety of solid particles which can be used to in the preparation of emulsions such as described above, and which include, but are not limited to, silica, microcrystalline cellulose, Laponite®, Humic acid, Eudragit® and latex particles.

What is claimed is:

1. A process for preparing granules, the process comprising the steps of:
    a) preparing an oil-in-water emulsion comprising
        i. a free, non-emulsified active substance selected from the group consisting of a flavour and a fragrance;
        ii. a water soluble biopolymer having a molecular weight below 100 KDa and devoid of emulsifying properties, and is present in an amount of from 10 to 70% by weight, relative to the total weight of the emulsion;
        iii. solid particles that are insoluble in water and hydrophilic; and
        iv. water;
        wherein the emulsion is free of emulsifiers; and
    b) spray-drying the emulsion obtained in step a) so as to obtain granules;
        wherein no emulsifier is added at any step of the process.

2. A process according to claim 1, wherein the active substance comprises at least 90% by weight, relative to the total weight of the active substance, of compounds having a log P of at least 1.

3. A process according to claim 1 wherein the flavour is used in an amount of from 5 to 67% by weight, relative to the total weight of the emulsion.

4. A process according to claim 1 wherein the water soluble biopolymer is a polysaccharide, oligosaccharide or disaccharide and is used in an amount of from 30 to 55% by weight, relative to the total weight of the emulsion.

5. A process according to claim 1, wherein the solid particles have an average diameter of at most 3 μm.

6. A process according to claim 1, wherein the solid particles are selected from the group consisting of
silicon oxides;
metal oxides, hydroxides, salts of inorganic or organic acids and their mixtures;
silver nanoparticles;
magnesium and aluminium silicates;
latexes;
dietary fibers;
yeast cells;
humic acid;
enteric polymers; and
crystals of fats or fatty acids.

7. A process according to claim 1, wherein the solid particles are silica particles.

8. A process according to claim 1, wherein the solid particles are used in an amount of from 0.1 to 30% by weight, relative to the total weight of the emulsion.

9. A process according to claim 1 wherein the ratio of solid particles to active substance is ranging between 1:1 and 1:30.

10. A process according to claim 1 wherein at least 5% by weight of the active agent having a vapour pressure of at least 0.007 Pa at 25° C.

11. A process according to claim 1 wherein the solid particles are in contact with the active substance.

12. A process according to claim 1 wherein the solid particles form a three phase contact angle, measured through the aqueous phase at an interface of water and oil at the particle surface, that is between 10 and 90 degrees.

13. A process according to claim 1 wherein the granules have a particle size of at least 10 μm to 750 μm.

14. A process according to claim 1 wherein the granules have a particle size of at least 20 μm to 300 μm.

* * * * *